United States Patent
Shiflett et al.

(10) Patent No.: US 12,157,719 B2
(45) Date of Patent: Dec. 3, 2024

(54) HALOALKANE SULFONIC ACIDS, COMPOSITIONS THEREOF, AND RELATED METHODS

(71) Applicant: University of Kansas, Lawrence, KS (US)

(72) Inventors: Mark Brandon Shiflett, Lawrence, KS (US); Rajkumar Kore, Lawrence, KS (US); Aaron M. Scurto, Oskaloosa, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 18/042,508

(22) PCT Filed: Aug. 20, 2021

(86) PCT No.: PCT/US2021/046835
§ 371 (c)(1),
(2) Date: Feb. 22, 2023

(87) PCT Pub. No.: WO2022/046540
PCT Pub. Date: Mar. 3, 2022

(65) Prior Publication Data
US 2023/0322663 A1 Oct. 12, 2023

Related U.S. Application Data

(60) Provisional application No. 63/069,299, filed on Aug. 24, 2020.

(51) Int. Cl.
C07C 309/06 (2006.01)
C07C 2/86 (2006.01)
(Continued)

(52) U.S. Cl.
CPC ............ *C07C 309/06* (2013.01); *C07C 2/868* (2013.01); *C07C 303/20* (2013.01); *C10L 1/1608* (2013.01)

(58) Field of Classification Search
CPC ....... C07C 2/86; C07C 303/20; C07C 303/06; C07C 309/06; C10L 1/16
See application file for complete search history.

(56) References Cited

U.S. PATENT DOCUMENTS 3,428,654 A  2/1969 Rubinfeld et al.
5,176,813 A  1/1993 Newby
(Continued)

FOREIGN PATENT DOCUMENTS

DE  11 2004 001 729 T5  10/2006
WO  WO 2018/104875 A1  6/2018
WO  WO 2019/224311 A1  11/2019

OTHER PUBLICATIONS

Peng Cui et al., "Ionic liquid enhanced alkylation of iso-butane and 1-butene," *Catalysis Today* (2013), 200; pp. 30-35.
(Continued)

*Primary Examiner* — Sharon Pregler
(74) *Attorney, Agent, or Firm* — Bell & Manning, LLC

(57) ABSTRACT

Haloalkane sulfonic acids and salts thereof are provided. In embodiments, a haloalkane sulfonic acid or salt thereof comprises an alkyl group, at least one sulfonic acid group, and one or more halogens selected from Cl, Br, I, and F, the haloalkane sulfonic acid having a total number of carbon atoms of from 2 to 9, and wherein if at least one F atom is present, the haloalkane sulfonic acid comprises at least one other halogen selected from Cl, Br, and I. Methods of making and using the haloalkane sulfonic acids/salts are also provided.

20 Claims, 6 Drawing Sheets

Schematic Example of Mono-Sulfonic Acid Synthesis

Schematic Example of Multi-Sulfonic Acid Synthesis 1,2-dichloroethane-1,2disulfonic acid

(51) Int. Cl.
*C07C 303/20* (2006.01)
*C10L 1/16* (2006.01)

(56) References Cited

U.S. PATENT DOCUMENTS

| | | | |
|---|---|---|---|
| 5,824,832 | A | 10/1998 | Sherif et al. |
| 7,683,209 | B2 | 3/2010 | Harmer et al. |
| 8,283,492 | B2 | 10/2012 | Harmer et al. |
| 8,524,965 | B2 | 9/2013 | Campbell et al. |
| 10,246,395 | B2 | 4/2019 | Rogers et al. |
| 10,301,233 | B2 | 5/2019 | Timken et al. |
| 11,634,385 | B2* | 4/2023 | Ott .................. C07C 303/06 562/118 |
| 2015/0273460 | A1 | 10/2015 | Buchbinder et al. |
| 2016/0060277 | A1 | 3/2016 | Aduri et al. |
| 2016/0168054 | A1 | 6/2016 | Kalnes et al. |
| 2023/0322646 | A1 | 10/2023 | Shiflett et al. |
| 2023/0322662 | A1 | 10/2023 | Shiflett et al. |
| 2023/0373893 | A1 | 11/2023 | Shiflett |

OTHER PUBLICATIONS

Wikipedia, "Lewis acids and bases." May 22, 2019; retrieved from https://en.wikipedia.org/w/index.php?title=Lewis_acids_and_bases&oldid=898242465;pp. 1-10.

Congzhen Qiao et al., "Benzene alkylation with long chain olefins catalyzed by ionic liquids: a review," Front. Chem. Eng. China 2008, 2(3): 346-352. DOI 10.1007/x11705-008-0045-9.

Yibo He et al., "Synthesis of efficient SBA-15 immobilized ionic liquid catalyst and its performance for Friedel-Crafts reaction," *Catalysis Today* 276 (2016) 112-120.

Rajkumar Kore et al., ZSM-5 Zeolite Nanosheets with Improved Catalytic Activity Synthesized Using a New Class of Structure-Directing Agents, *Chemistry A European Journal* 2014, 20, 1-12. DOI: 10.1002/chem.201402665.

Rajkumar Kore et al., "Synthesis of Dicationic Ionic Liquids and their Application in the Preparation of Hierarchical Zeolite Beta," *Chemistry A European Journal* 2011, 17, 14360-14365. DOI: 10.1002/chem.201102946.

Rajkumar Kore et al., "Replacing HF or AlCl3 in the Acylation of Isobutylbenzene with Chloroaluminate Ionic Liquids," *ACS Sustainable Chem. Eng.* 2020, 8, 10330-10334.

The International Search Report and Written Opinion issued on Dec. 20, 2021 for international patent application No. PCT/US21/46835; pp. 1-11.

PubChem Schembl8746862. SID 234224885. PubChem Entry (online). National Center for Biotechnology Information. Dec. 2, 2015 [retrieved on Nov. 4, 2021]. Retrieved from the Internet: [URL: https://pubchem.ncbi.nlm.nih.gov/substance/234224885].

Campaigne, E. et al.,"Simultaneous Vicinal Dichlorination," *J. Am. Chem. Soc.* 1950, 72, 1, 629-630.

Branko Popov et al., "Galvanostatic Pulse and Pulse Reverse Plating of Zinc-Nickel Alloys from Sulfate Electrolytes on a Rotating Disc Electrode," *Journal of the Chemical Society, Faraday Transactions*. 1996, vol. 92, No. 20; pp. 1-9.

Jose M. Hidalgo et al., "Current uses and trends in catalytic isomerization, alkylation and etherification processes to improve gasoline quality," *Cent. Eur. J. Chem.* 12(1), 2014; pp. 1-13 DOI: 10.2478/s11532.013.0354-9.

Lenneman, WL et al.,"Sulfuric acid-catalyzed alkylation of Benzene with high molecular weigh alkanes," *Journal of Organic Chemistry*. 1954, vol. 19, No. 3; pp. 1-2.

Davood Habibi et al.,"Acetylation of Phenols, Anilines, and Thiols Using Silica Sulfuric Acid under Solvent-Free Conditions," *Journal of Chemistry*. 2013, vol. 2013, Article ID 268654; pp. 1-7.

Norman C. Foster et al., "Sulfonation and Sulfation Processes," 1997 [retrieved on Nov. 4, 2021]. Retrieved from Internet {URL: http://www.chemithon.com/Resources/pdgs/Technical_papers/Sulfo%20and%20Sulfa%201.pdf].

* cited by examiner

PYRIDINIUM

PYRIDAZINIUM

PYRIMIDINIUM

PYRAZINIUM

IMIDAZOLIUM

PYRAZOLIUM

THIAZOLIUM

OXAZOLIUM

CATIONS:

FORMULA A $[C_{R1}C_n im]^+$ (n=0-18; R1=H OR ALKYL GROUP)

FORMULA B $[C_{R1}Im-C_n-SO_3H]^+$ (n=0,3,4,5; R1=H OR ALKYL GROUP)

FORMULA C $[X_{R1R2R3}-C_n-SO_3H]^+$ (n=0,3,4,5; X=N,P,S; $R_1/R_2/R_3$=H, ALKYL GROUP)

FORMULA D

[PYRIDINIUM]$^+$ $R_2/R_3/R_4$=H, ALKYL GROUP $R_1$=H, ALKYL GROUP, $C_n$-SO$_3$H(n=0,3,4,5)

FORMULA E (n=0,1; m=0,1,2)
$R_1/R_2/$=H, ALKYL GROUP
,$C_n$-SO$_3$H(n=0,3,4,5)

BASES:

FORMULA F n=0 TO 18

FORMULA G n=0,3,4,5

FORMULA H n=0,3,4,5; X=N,P,S;
$R_1/R_2$=H, ALKYL GROUP

FORMULA I $R_2/R_3/R_4$=H, ALKYL GROUP

FORMULA J n=0,1; m=0,1,2
$R_1$=H, ALKYL GROUP,
$C_n$-$SO_3H$(n=0,3,4,5)

BENZENE    TOLUENE    o/m/p-XYLENES    MESITYLENE    HEXAMETHYLBENZENE

HALOALKANE SULFONIC ACIDS, COMPOSITIONS THEREOF, AND RELATED METHODS

CROSS-REFERENCE TO RELATED APPLICATIONS

The present application is a National Stage of International Application No. PCT/US21/46835, filed Aug. 20, 2021, which claims priority to U.S. provisional patent application No. 63/069,299, that was filed Aug. 24, 2020, the entire contents of both of which are incorporated herein by reference.

BACKGROUND

Sulfuric acid ($H_2SO_4$), a strong acid, finds use in many applications, e.g., catalyzing the conversion of cyclohexanone oxime to caprolactam (an intermediate in the production of nylon) to catalyzing the alkylation of isobutane in the production of motor fuel. Fluoroalkane sulfonic acids have been developed in order to increase the acidity of sulfuric acid. The processes used to synthesize the fluoroalkane sulfonic acids require electrochemistry, increasing the cost and limiting the availability of such acids.

SUMMARY

The present disclosure provides new haloalkane sulfonic acids and processes for their preparation. Ionic liquids and catalyst compositions based on the haloalkane sulfonic acids are also provided, as well as applications for the haloalkane sulfonic acids and compositions thereof.

In embodiments, a haloalkane sulfonic acid or a salt thereof comprises an alkyl group, at least one sulfonic acid group, and one or more halogens selected from Cl, Br, I, and F, the haloalkane sulfonic acid having a total number of carbon atoms of from 2 to 9, and wherein if at least one F atom is present, the haloalkane sulfonic acid comprises at least one other halogen selected from Cl, Br, and I. Processes for making and using the haloalkane sulfonic acids/salts are also provided.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

DETAILED DESCRIPTION

Figure 1A:
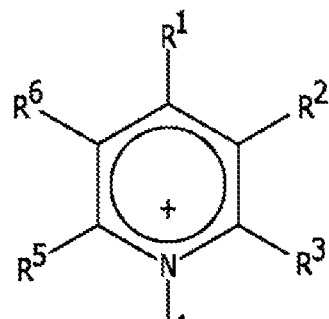
FIGS. 1A-1C show illustrative cations which may be used to form an ionic liquid for use in catalyst compositions comprising the present haloalkane sulfonic acids or for forming an ionic liquid from the present haloalkane sulfonic acids.
Figure 1A:
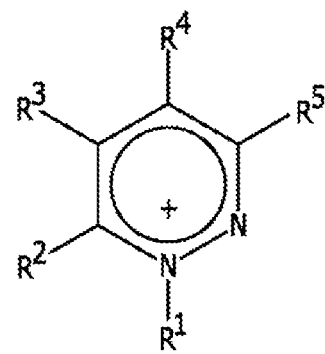
Figure 1A:
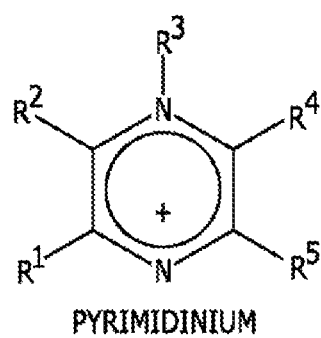
Figure 1A:
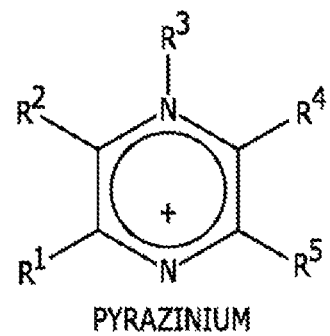
Figure 1A:
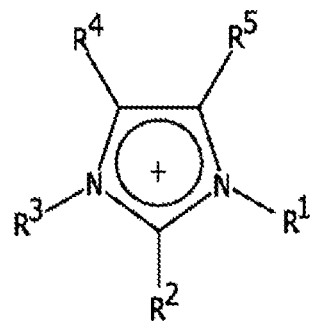
Figure 1A:
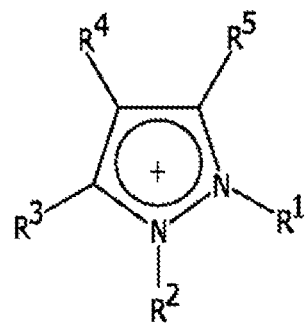
Figure 1A:
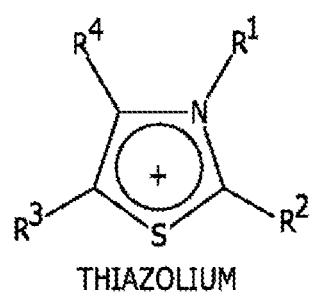
Figure 1A:
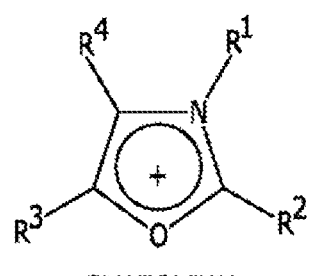

The present disclosure provides new haloalkane sulfonic acids and processes for their preparation. Compositions based on the haloalkane sulfonic acids are also provided, as well as applications for the haloalkane sulfonic acids and compositions thereof. The present haloalkane sulfonic acids span a wide range of acidity and solubility, rendering them useful for a variety of applications requiring an acid. Single-step processes of making the haloalkane sulfonic acids are also provided, which are more simple and cheaper than existing processes of making fluoroalkane sulfonic acids. The present haloalkane sulfonic acids may also be used to form ionic liquids with advantageous properties related to the haloalkane sulfonate anion component, e.g., as compared to existing halogenated anions. These properties include the surprising miscibility of certain haloalkane sulfonic acids, including chloroalkane mono-sulfonic acids (e.g., tetrachloroethane mono-sulfonic acid), in hydrocarbons. This result is completely unexpected since known fluoroalkane mono-sulfonic acids (e.g., tetrafluoroethane mono-sulfonic acid) are immiscible in hydrocarbons (e.g., isobutane, butene). The resulting ionic liquids may be used in a variety of applications requiring an ionic liquid.

Haloalkane Sulfonic Acids

The present disclosure provides certain haloalkane sulfonic acid compounds. Although one or more provisos (described below) may apply, in general, the "haloalkane sulfonic acid" comprises an alkyl group, a sulfonic acid group, and a halogen. The alkyl group may have from 1 to 9 carbon atoms. This encompasses alkyl groups having 2, 3, 4, 5, 6, 7, 8, or 9 carbon atoms, i.e., the alkyl group may be an ethyl, propyl, butyl, etc. The alkyl group may be linear, cyclic, or branched. The sulfonic acid group (—$SO_3H$) is covalently bound to a carbon of the alkyl group and the halogen (—X) is bound to this carbon or another carbon of the alkyl group. One or more than one sulfonic acid group may be present in the haloalkane sulfonic acid. Thus, both haloalkane mono-sulfonic acids (a single sulfonic acid group) and haloalkane multi-sulfonic acids (more than one sulfonic acid group) are encompassed. In embodiments, the number of sulfonic acid groups in the haloalkane sulfonic acid is one, two, three, etc. Similarly, one or more than one halogen may be present in the haloalkane sulfonic acid. In embodiments, the number of halogens is one, two, three, four, five, six, etc. The halogen atom(s) may be selected from Cl, Br, I, and F. However, in embodiments, if at least one F is present, another non-fluorine halogen is also present, e.g., Cl, Br, I. In other embodiments, no F is present. In embodiments, the haloalkane sulfonic acid is a chloroalkane sulfonic acid (i.e., chlorine is the only halogen present). In embodiments, the haloalkane sulfonic acid is a chloroalkane mono-sulfonic acid.

In embodiments, the haloalkane sulfonic acid comprises an alkyl group selected from methyl, ethyl, propyl, and butyl; one, two, or three sulfonic acid groups; and one or more halogens selected from Cl, Br, I, and F, wherein if at least one F atom is present, the haloalkane sulfonic acid comprises at least one other halogen selected from Cl, Br, and I. In this embodiment, variations may apply such as one or more of: the alkyl group is selected from ethyl, propyl, and butyl; one or two sulfonic acid groups are present; the one or more halogens are selected from Cl, Br, and I; and the one or more halogens are selected from Cl and Br.

In embodiments, the haloalkane sulfonic acid has the formula $CR_3$—$CR_2$—$SO_3H$, wherein each R is independently selected from hydrogen, $C_nR'_{(2n+1)}$, $C_nR'_{(2n-1)}$, $SO_3H$, and a halogen; n is 0 to 7; each R' is independently selected from hydrogen, $SO_3H$, and a halogen; at least one R or at least one R' is a halogen selected from Cl, Br, I, and F; if at least one R or at least one R' is F and a single $SO_3H$ is present, then at least another R or at least another R' is a halogen selected from Cl, Br, and I; and wherein the haloalkane sulfonic acid has a total number of carbon atoms of from 2 to 9. The formula $C_nR'_{(2n+1)}$ encompasses both linear and branched structures while the formula $C_nR'_{(2n-1)}$ encompasses cyclic structures. In this embodiment, one or more provisos may apply such as: each R is independently selected from H, $C_nR'_{(2n+1)}$, $C_nR'_{(2n-1)}$, $SO_3H$, Cl, Br, and I and each R' is independently selected from H, $SO_3H$, Cl, Br, and I; each R is independently selected from hydrogen, $C_nR'_{(2n+1)}$, $SO_3H$, and a halogen; n is 0, 1, or 2; the total number of carbons is from 2 to 4; at least two $SO_3H$ are present; and two or three $SO_3H$ are present.

In embodiments, the haloalkane sulfonic acid has the formula $C_nR_{(2n+1)}$—$CR_2$—$CR_2$—$SO_3H$, wherein n is 0 to 7; each R is independently selected from hydrogen, $SO_3H$, and a halogen; at least one R is a halogen selected from Cl, Br, I, and F; and wherein if at least one R is F and a single $SO_3H$ is present, then at least another R is a halogen selected from Cl, Br, and I. The formula $C_nR_{(2n+1)}$ encompasses both linear and branched structures. In this embodiment, one or more provisos may apply such as: n is 0, 1, or 2; each R is independently selected from H, Cl, Br, I and $SO_3H$; at least two $SO_3H$ are present; two or three $SO_3H$ are present; each R is independently selected from H, Cl, Br, and I; and each R is independently selected from H, Cl, and Br.

In embodiments, the haloalkane sulfonic acid has the formula $CR_2(SO_3H)$—$CR_2$—$SO_3H$, wherein each R is independently selected from hydrogen, $C_nR'_{(2n+1)}$, $C_nR'_{(2n-1)}$, $SO_3H$, and a halogen selected from Cl, Br, I, and F; n is from 0 to 7; each R' is independently selected from hydrogen, $SO_3H$, and a halogen selected from Cl, Br, I, and F; at least one R or at least one R' is the halogen; and wherein the haloalkane sulfonic acid has a total number of carbon atoms from 2 to 9. The formula $C_nR'_{(2n+1)}$ encompasses both linear and branched structures while the formula $C_nR'_{(2n-1)}$ encompasses cyclic structures. In this embodiment, one or more provisos may apply such as: each R is independently selected from hydrogen, $C_nR'_{(2n+1)}$, $SO_3H$, and a halogen selected from Cl, Br, I, and F; n is 0, 1, or 2; the total number of carbons is from 2 to 4; the halogen is F; at least three $SO_3H$ are present; and two or three $SO_3H$ are present.

In embodiments, the haloalkane sulfonic acid has the formula $C_nR_{(2n+1)}$—$CR(SO_3H)$—$CR_2$—$SO_3H$, wherein n is 0 to 7; each R is independently selected from hydrogen, $SO_3H$, and a halogen selected from Cl, Br, I, and F; and wherein at least one R is the halogen. In this embodiment, one or more provisos may apply such as: n is 0, 1, or 2; the halogen is F; at least three $SO_3H$ are present; and two or three $SO_3H$ are present.

Any of the present haloalkane sulfonic acids comprising fluorine may be characterized by a ratio of non-fluorine halogen (e.g., Cl, Br, I, or combinations thereof) to fluorine. In embodiments, the ratio is at least 0.4, at least 0.6, at least 0.8, at least 1, at least 2, at least 3, or in a range of based on any of these values.

Illustrative haloalkane sulfonic acids include the following: tetrachloroethane sulfonic acid ($HCCl_2$—$CCl_2$—$SO_3H$); tetrabromoethane sulfonic acid ($HCBr_2$—$CBr_2$—$SO_3H$); tetraiodooethane sulfonic acid ($HCI_2$—$CI_2$—$SO_3H$); 1,2-dichloroethanesulfonic acid ($CH_2Cl$—$CHCl$—$SO_3H$); 1,2-dichlorobutanesulfonic acid ($CH_3$—$CH_2$—$CHCl$—$CHCl$—$SO_3H$); 1,2-dichloro-1,2-difluoroethanesulfonic acid ($HCFCl$—$CFCl$—$SO_3H$); hexachloropropanesulfonic acid ($CCl_3$—$CHCl$—$CCl_2$—$SO_3H$); chloroethane sulfonic acid ($CH_2Cl$—$CH_2$—$SO_3H$); trichloroethane sulfonic acid ($CH_2Cl$—$CCl_2$—$SO_3H$ or $CHCl_2$—$CHCl$—$SO_3H$); and trichlorofluoroethane sulfonic acid ($CHCl_2$—$CFCl$—$SO_3H$).

Illustrative haloalkane sulfonic acids also include the following: $HCCl(SO_3H)$—$CHCl(SO_3H)$ (1,2-dichloroethane-1,2-disulfonic acid); $CH_3$—$CH_2$—$CH(SO_3H)$—$CHCl(SO_3H)$ (1-chlorobutane-1,2-disulfonic acid); $CH_3$—$CH(SO_3H)$—$CHCl(SO_3H)$ (1-chloropropane-1,2-disulfonic acid); $CF_3$—$CH(SO_3H)$—$CHCl(SO_3H)$ (1-chloro-3,3,3-trifluoropropane-1,2-disulfonic acid); 2-chloroethane-1,1,2-trisulfonic acid ($CH(SO_3H)_2$—$CHCl(SO_3H)$); 1,1,2-trichloroethane-1,2-disulfonic acid ($CCl_2(SO_3H)$—$CHCl$—$SO_3H$); 2-fluoropropane-1,2-disulfonic acid ($CH_3$—$CF(SO_3H)$—$CH_2(SO_3H)$); 3,3,3-trifluoropropane-1,2-disulfonic acid ($CF_3$—$CH(SO_3H)$—$CH_2(SO_3H)$); 3,3,3-trifluoropropane-1,1,2-trisulfonic acid ($CF_3$—$CH(SO_3H)$—$CH(SO_3H)_2$); 1,2-difluoroethane-1,1,2-trisulfonic acid ($CHF(SO_3H)$—$CF(SO_3H)_2$); $CH(SO_3H)_2$—$CCl(SO_3H)_2$.

In embodiments, the following haloalkane sulfonic acids are excluded: triflic acid ($CF_3SO_3H$), tetrafluoroethanesulfonic acid ($HCF_2$—$CF_2$—$SO_3H$), and 2-chloro, 1,1,2-trifluoroethanesulfonic acid. However, the present disclosure also provides one-step processes for making such haloalkane sulfonic acids.

The unprotonated form the disclosed haloalkane sulfonic acids (i.e., the haloalkane sulfonates) are also encompassed. Salts (e.g., alkali salts such as sodium or potassium) of the disclosed haloalkane sulfonic acids are also encompassed. In embodiments, a salt of the haloalkane sulfonic acid may be used in place of the haloalkane sulfonic acid.

Processes for Preparing Haloalkane Sulfonic Acids

Figure 4A:
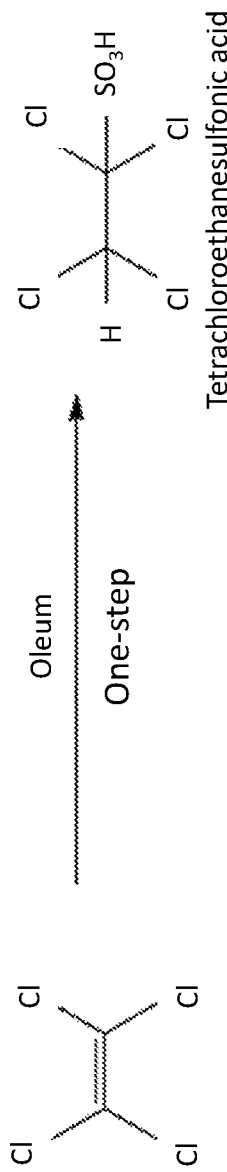
FIGS. 4A-4B show schematics of a one-step process which may be used to prepare the present haloalkane sulfonic acids, including mono-sulfonic acids (FIG. 4A) and multi-sulfonic acids (FIG. 4B), using tetrachloroethene and its conversion to tetrachloroethane sulfonic acid as an illustrative example.
Figure 4B:
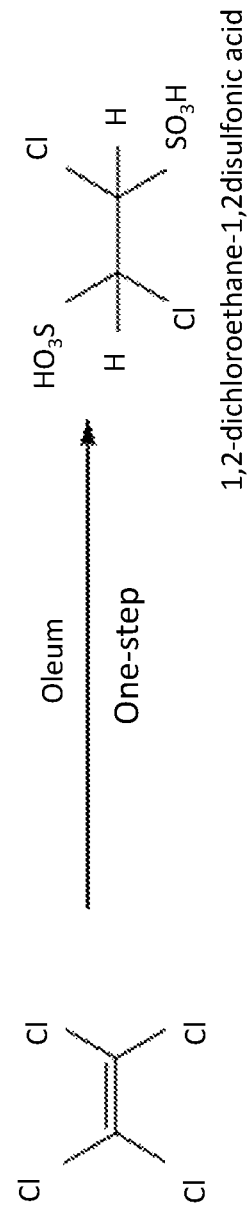

FIGS. 4A and 4B are schematics illustrating a one-step process which may be used to prepared the present haloalkane sulfonic acids. The one-step process is illustrated using tetrachloroethylene, but in general, any haloalkene may be used, depending upon the desired haloalkane. That is, the haloalkene to be used corresponds to the haloalkane to be prepared, e.g., 1,2-dichloro-1,2-difluoroethylene is a haloalkene which may be used to provide 1,2-dichloro-1,2-difluoroethane.

By "one-step," it is meant that the haloalkene is converted to the haloalkane sulfonic acid(s) in a single synthetic step. This is by contrast to conversion to a salt, followed by a second acidification step to exchange the cation of the salt for a proton/acid. However, this does not preclude additional step(s) to otherwise process or recover the haloalkane sulfonic acid(s) from the reaction mixture. An embodiment of a one-step process comprises combining the selected haloalkene with oleum or 98% sulfuric acid under conditions to react $H_2SO_4$ with the carbon-carbon double-bond of the haloalkene. The reaction may result in the production of both a haloalkane mono-sulfonic acid and one or more haloalkane multi-sulfonic acids. By "oleum," it is meant sulfuric acid ($H_2SO_4$) containing sulfur trioxide ($SO_3$). One or more solvents may be used, but this is not necessary. Thus, an additional advantage of the one-step process is that it may be carried out without using any solvent, i.e., the process is solventless.

The term "conditions" may refer to the amount of $SO_3$ in the oleum; the use of, or absence of, a solvent(s); the ratio of oleum:haloalkene (or 98% sulfuric acid:haloalkene); the temperature; and the time. In general, values of these parameters may be selected to ensure reaction and to adjust the number of $SO_3H$ groups added to the haloalkene (i.e., tune selectivity to haloalkane mono- or multisulfonic acids). However, the amount of $SO_3$ in the oleum may be in a range of from 5% to 60%, from 10% to 50%, or from 20% to 30% (each of these values is equivalent/mole percent). The ratio of oleum:haloalkene (or 98% sulfuric acid:haloalkene) may be in a range of from 0.1 to 10, from 0.2 to 10, or from 0.5 to 10 (each of these values is equivalent/mole ratio). The temperature may be in a range of from 25° C. to 140° C. The time may be in a range of from 5 to 72 hours. If a combination of haloalkane mono- and multi-sulfonic acid(s) are produced, they may be separated from one another, e.g., via distillation. The one-step process is further described in the Examples below, using illustrative halolalkenes and illustrative conditions.

Catalyst Compositions of the Haloalkane Sulfonic Acids

Although the present haloalkane sulfonic acids may be used by themselves in a variety of applications requiring an acid, they may also be combined with other components to form certain catalyst compositions. Illustrative compositions are shown in Table 1, below. More than one type of each component may be used, i.e., more than one type of ionic liquid, more than one type of haloalkane sulfonic acid, more than one type of Lewis acid, more than one type of base, and/or more than one type of aromatic. In other such embodiments, a single type of each component may be used. Any of the haloalkane sulfonic acids described above may be used as the "Haloalkane Sulfonic Acid" component. A description of each of the remaining components in Table 1 immediately follows.

TABLE 1

Compositions comprising haloalkane sulfonic acids.

$[IL]_x$-[Haloalkane Sulfonic Acid]$_{(100-x)}$
$[IL]_x$-[Haloalkane Sulfonic Acid]$_{(100-x)}$-[Aromatic]$_y$
$[Lewis Acid]_x$-[Haloalkane Sulfonic Acid]$_{(100-x)}$
$[Base]_x$-[Haloalkane Sulfonic Acid]$_{(100-x)}$
$[Base]_x$-[Haloalkane Sulfonic Acid]$_{(100-x)}$-[Aromatic]$_y$ Ionic Liquids Various ionic liquids may be used as a component of a catalyst composition comprising any of the disclosed haloalkane sulfonic acids. As used in the present disclosure, "ionic liquid" refers to salts composed of at least one cation and at least one anion and are being used in their fluid state. They are generally in their fluid state at or below a temperature of about 100° C.

Representative examples of ionic liquids suitable for use herein are included among those that are described in sources such as *J. Chem. Tech. Biotechnol.*, 68:351-356 (1997); *Chem. Ind.*, 68:249-263 (1996); *J. Phys. Condensed Matter*, 5: (supp 34B):899-8106 (1993); *Chemical and Engineering News*, Mar. 30, 1998, 32-37; *J. Mater. Chem.*, 8:2627-2636 (1998); *Chem. Rev.*, 99:2071-2084 (1999); and WO 05/113,702 (and references cited therein), each of which is by this reference incorporated herein for the purpose of the ionic liquids disclosed therein.

Many ionic liquids are formed by reacting a nitrogen-containing heterocyclic ring, preferably a heteroaromatic ring, with an alkylating agent (e.g., an alkyl halide) to form a quaternary ammonium salt, and performing ion exchange or other suitable reactions with various Lewis acids or their conjugate bases to form the ionic liquid. Some ionic liquids are formed by reacting N-, P-, and S-compounds with a Bronsted acid to quaternize the heteroatom. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but the alkyl groups are preferably $C_{1-16}$ groups. Various trialkylphosphines, thioethers and cyclic and non-cyclic quaternary ammonium salts may also be used for this purpose. Ionic liquids suitable for use herein may also be synthesized by salt metathesis, by an acid-base neutralization reaction, or by quaternizing a selected nitrogen-containing compound. The synthesis of other ionic liquids suitable for use herein is described in U.S. Pat. No. 8,715,521, which is by this reference incorporated in its entirety as a part hereof for all purposes. Ionic liquids may also be obtained commercially from several companies such as Merck (Darmstadt, Germany), BASF (Mount Olive N.J.), Fluka Chemical Corp. (Milwaukee Wis.), and Sigma-Aldrich (St. Louis Mo.).

Ionic liquids suitable for use herein comprise a cation and an anion. A variety of cations and anions may be used. Either or both of the ions may be fluorinated. However, in embodiments, neither of the ions are fluorinated. The ionic liquid may include more than one type of cation, more than one type of anion, or both. However, the ionic liquid may include a single type of cation and a single type of anion. When the ionic liquid includes a single type of cation and a single type of anion, however, this does not preclude some amount of ion exchange with other ions in the catalyst composition (derived from other components of the catalyst composition).

Figure 1B:
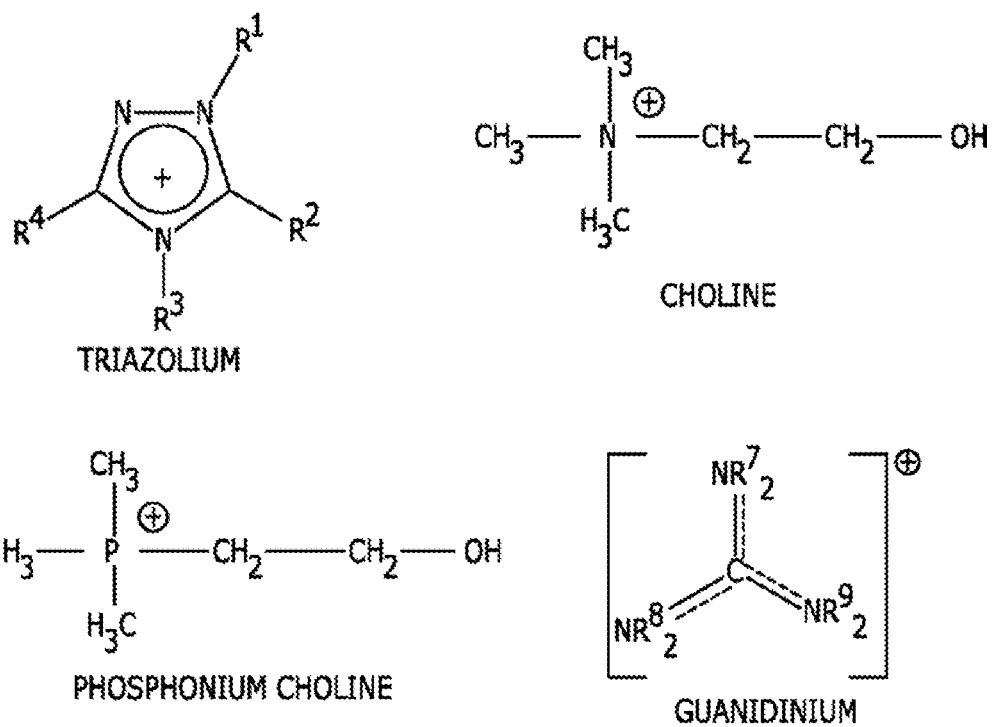
Figure 1C:
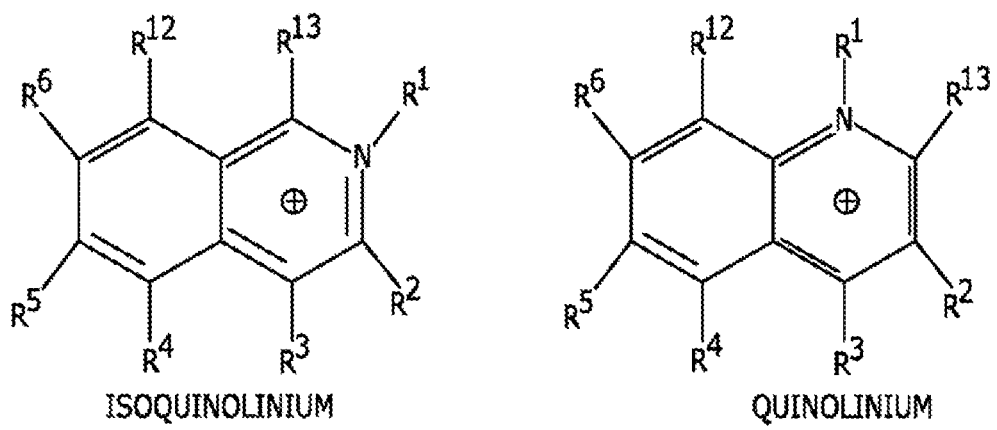
Figure 1C:
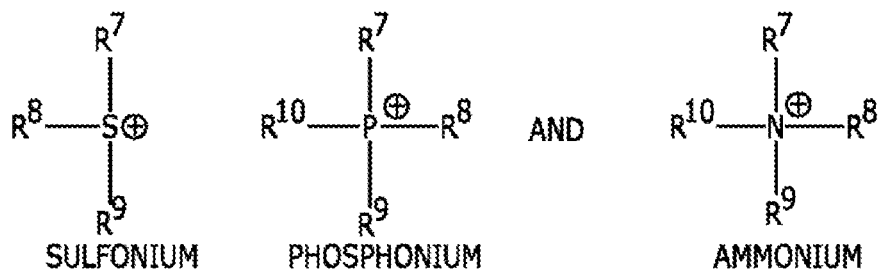

In embodiments, the cation is selected from the group consisting of cations represented by the structures of the formulae shown in FIGS. 1A-1C. In these formulae, the following provisos apply:

(a) $R^1$, $R^2$, $R^3$, $R^4$, $R^5$, $R^6$, $R^{12}$ and $R^{13}$ are independently selected from the group consisting of:
(i) H;
(ii) halogen such as F;
(iii) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ SH, and $SO_3H$;
(iv) —$CH_3$, —$C_2H_5$, or $C_3$ to $C_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, $NH_2$ and SH;
(v) $C_6$ to $C_{25}$ unsubstituted aryl, or $C_6$ to $C_{25}$ unsubstituted heteroaryl, groups having one to three heteroatoms independently selected from the group consisting of O, N, Si and S, wherein the unsubstituted aryl or unsubstituted heteroaryl may be bonded to the structure via an alkyl (e.g., —$CH_2$—) spacer group;
(vi) $C_6$ to $C_{25}$ substituted aryl, or $C_6$ to $C_{25}$ substituted heteroaryl, groups having one to three heteroatoms independently selected from the group consisting of O, N, Si and S; wherein the substituted aryl or substituted heteroaryl may be bonded to the structure via an alkyl (e.g., —$CH_2$—) spacer group; and wherein said substituted aryl or substituted heteroaryl has one to three substituents independently selected from the group consisting of:
(A) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ and SH,
(B) OH,
(C) $NH_2$, and
(D) SH; and
(vii) —$(CH_2)_nSi(CH_2)_mCH_3$, —$(CH_2)_nSi(CH_3)_3$, —$(CH_2)_nOSi(CH_3)_m$, where n is independently 1-4 and m is independently 0-4;
(b) $R^7$, $R^8$, $R^9$, and $R^{10}$ are independently selected from the group consisting of:
(i) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$, SH and $SO_3H$;
(ii) $CH_3$, —$C_2H_5$, or $C_3$ to $C_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, $NH_2$ and SH;
(iii) $C_6$ to $C_{25}$ unsubstituted aryl, or $C_6$ to $C_{25}$ unsubstituted heteroaryl, groups having one to three heteroatoms independently selected from the group consisting of O, N, Si and S; and
(iv) $C_6$ to $C_{25}$ substituted aryl, or $C_6$ to $C_{25}$ substituted heteroaryl, groups having one to three heteroatoms independently selected from the group consisting of O, N, Si and S, and wherein the substituted aryl or substituted heteroaryl group has one to three substituents independently selected from the group consisting of:
(A) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ and SH,
(B) OH,
(C) $NH_2$, and
(D) SH; and
(v) —$(CH_2)_nSi(CH_2)_mCH_3$, —$(CH_2)_nSi(CH_3)_3$, —$(CH_2)_nOSi(CH_3)_m$, where n is independently 1-4 and m is independently 0-4; and
(c) optionally, at least two of $R^1$, $R^2$, $R^3$, $R^4$, $R^5$, $R^6$, $R^7$, $R^8$, $R^9$, and $R^{10}$ can together form a cyclic or bicyclic alkyl or alkenyl group.

In embodiments, the ionic liquid comprises a cation selected from one or more members of the group consisting of pyridinium, pyridazinium, pyrimidinium, pyrazinium, imidazolium, pyrazolium, thiazolium, oxazolium, triazolium, phosphonium, ammonium, benzyltrimethylammonium, choline, cholinium, dimethylimidazolium, guanidinium, phosphonium choline, lactam, sulfonium, tetramethylammonium, and tetramethylphosphonium.

In embodiments, the ionic liquid comprises an anion selected from one or more members of the group consisting of: $[CH_3CO_2]^-$, $[HSO_4]^-$, $[CH_3OSO_3]^-$, $[C_2H_5OSO_3]^-$, $[CH_3C_6H_4SO_3]^-$ ($[TSO]^-$), $[AlCl_4]^-$, $[Al_2Cl_7]^-$, $[ZnCl_4]^{2-}$, $[Zn_2Cl_6]^{2-}$, $[Zn_3Cl_8]^{2-}$, $[FeCl_4]^-$, $[GaCl_4]^-$, $[Ga_2Cl_7]^-$, $[InCl_4]^-$, $[In_2Cl_7]^-$, $[CO_3]^{2-}$, $[HCO_3]^-$, $[NO_2]^-$, $[NO_3]^-$, $[SO_4]^{2-}$, $[PO_3]^{3-}$, $[HPO_3]^{2-}$, $[H_2PO_3]^{1-}$, $[PO_4]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, carborates optionally substituted with alkyl or substituted alkyl; carboranes optionally substituted with alkylamine, substituted alkylamine, alkyl or substituted alkyl; and a fluorinated anion.

In embodiments, the ionic liquid comprises an anion selected from one or more members of the group consisting of aminoacetate, ascorbate, benzoate, catecholate, citrate, dimethylphosphate, formate, fumarate, gallate, glycolate, glyoxylate, iminodiacetate, isobutyrate, kojate, lactate, levulinate, oxalate, pivalate, propionate, pyruvate, salicylate, succinamate, succinate, tiglate, tetrafluoroborate, tetrafluoroethanesulfonate, tropolonate, $[CH_3CO_2]^-$, $[HSO_4]^-$, $[CH_3SO_3]^-$, $[CH_3OSO_3]^-$, $[C_2H_5OSO_3]^-$, $[CH_3C_6H_4SO_3]^-$, $[AlCl_4]^-$, $[Al_2Cl_7]^-$, $[ZnCl_4]^{2-}$, $[Zn_2Cl_6]^{2-}$, $[Zn_3Cl_8]^{2-}$, $[FeCl_4]^-$, $[GaCl_4]^-$, $[Ga_2Cl_7]^-$, $[InCl_4]^-$, $[In_2Cl_7]^-$, $[CO_3]^{2-}$, $[HCO_3]^-$, $[NO_2]^-$, $[NO_3]^-$, $[SO_4]^{2-}$, $[PO_3]^{3-}$, $[HPO_4]^{2-}$, $[H_2PO_4]^-$, $[HSO_3]^-$, $[CuCl_2]^-$, $Cl^-$, $Br^-$, $I^-$, $SCN^-$, $[BF_4]^-$, $[PF_6]^-$, $[SbF_6]^-$, $[CF_3SO_3]^-$, $[HCF_2CF_2SO_3]^-$, $[CF_3HFCCF_2SO_3]^-$, $[CHF_2CF_2SO_3]^-$, $[HCClFCF_2SO_3]^-$, $[(CF_3SO_2)_2N]^-$, $[(CF_3CF_2SO_2)_2N]^-$, $[(CF_3SO_2)_3C]^-$, $[CF_3CO_2]^-$, $[CF_3OCFHCF_2SO_3]^-$, $[CF_3CF_2OCFHCF_2SO_3]^-$, $[CF_3CFHOCF_2CF_2SO_3]^-$, $[CF_2HCF_2OCF_2CF_2SO_3]^-$, $[CF_2ICF_2OCF_2CF_2SO_3]$, $[CF_3CF_2OCF_2CF_2SO_3]^-$, $[(CF_2HCF_2SO_2)_2N]—$, $[(CF_3CFHCF_2SO_2)_2N]^-$, $[N(CN)_2]$, $F^-$, and anions represented by the structure of the following formula, $[R_{11}COO]^-$, wherein $R^{11}$ is selected from the group consisting of:
(i) —$CH_3$, —$C_2H_5$, or $C_3$ to $C_{10}$ straight-chain, branched or cyclic alkane or alkene groups, optionally substituted with at least one member selected from the group consisting of Cl, Br, F, I, OH, $NH_2$ and SH;
(ii) —$CH_3$, —$C_2H_5$, or $C_3$ to $C_{10}$ straight-chain, branched or cyclic alkane or alkene groups that contain one to three heteroatoms selected from the group consisting of O, N, Si and S, and are optionally substituted with at least one member selected from the group consisting of Cl, Br, F, I, OH, $NH_2$ and SH;
(iii) $C_6$ to $C_{10}$ unsubstituted aryl, or $C_6$ to $C_{10}$ unsubstituted heteroaryl, groups having one to three heteroatoms independently selected from the group consisting of O, N, Si and S; and
(iv) $C_6$ to $C_{10}$ substituted aryl, or $C_6$ to $C_{10}$ substituted heteroaryl, groups having one to three heteroatoms independently selected from the group consisting of O, N, Si and S; and wherein the substituted aryl or substituted heteroaryl group has one to three substituents independently selected from the group consisting of:
(A) —$CH_3$, —$C_2H_5$, or $C_3$ to $C_{10}$ straight-chain, branched or cyclic alkane or alkene groups, optionally substituted with at least one member selected from the group consisting of Cl, Br, F, I, OH, $NH_2$ and SH,
(B) OH,
(C) $NH_2$, and
(D) SH.

Figure 1D:
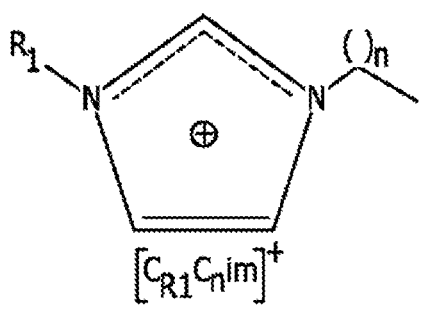
FIG. 1D shows illustrative cations which may be used to form an ionic liquid for use in catalyst compositions comprising the present haloalkane sulfonic acids or for forming an ionic liquid from the present haloalkane sulfonic acids.
Figure 1D:
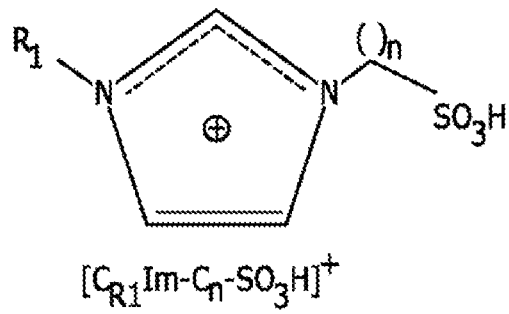
Figure 1D:
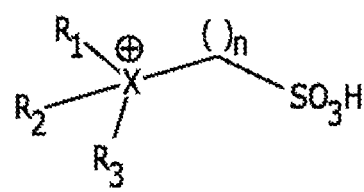
Figure 1D:
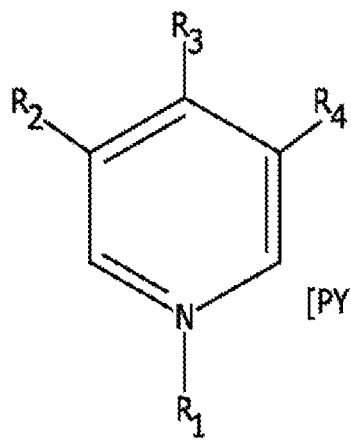
Figure 1D:
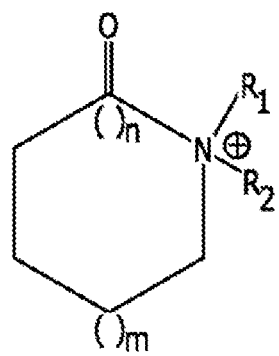

In embodiments, the cation of the ionic liquid is selected from an imidazolium, an ammonium, a phosphonium, a sulfonium, a pyridinium, and a lactam. The cation may be protic or aprotic. The proton in the protic cation may be from a —$SO_3H$ group. Illustrative imidazolium, ammonium, phosphonium, sulfonium, pyridinium, and lactam cations are shown in FIG. 1D. In embodiments, the cation of the ionic liquid is selected from the group consisting of cations represented by the structures of the formulae shown in FIG. 1D, i.e., Formulae A-E. In these formulae, the provisos noted in FIG. 1D apply.

The anion of the ionic liquid may be a sulfonate. The sulfonate may have the formula $[R-SO_3]^-$, wherein R is an alkyl group or an aryl group. The alkyl group may be a linear alkyl group in which the number of carbons may range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom such as F. Aryl groups may be unsubstituted or substituted as described above with respect to alkyl groups. However, substituted aryl groups also refer to an unsubstituted monocyclic aryl group in which one or more carbon atoms are bonded to an alkane. The alkane may be linear, have various numbers of carbon, and may be unsubstituted or substituted as described above with respect to alkyl groups.

Figure 2:
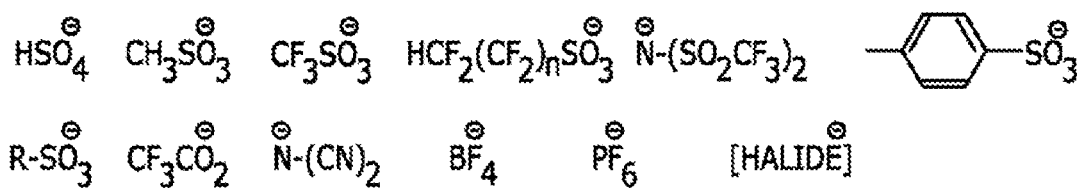
FIG. 2 shows illustrative anions which may be used to form an ionic liquid for use in catalyst compositions comprising the present haloalkane sulfonic acids.

The anion may be a carboxylate. The carboxylate may have the formula $[R-CO_2]^-$, wherein R is an alkyl group as described above with respect to sulfonate. This means that fluoroalkane carboxylates are encompassed, e.g., R may be $CF_3$, $HCF_2CF_2$, $CF_3HFCCF_2$, etc. The carboxylate (or fluoroalkane carboxylate) may be a dicarboxylate, a tricarboxylate, a tetracarboxylate, etc. Other anions which may be used include $[HSO_4]$, dicyanamide; and inorganic anions such as $[BF_4]^-$, $[PF_6]^-$, and a halide. Illustrative anions are shown in FIG. 2. In $[HCF_2(CF_2)_nSO_3]^-$, n may be 0, 1, 2, or 3.

Ionic liquids disclosed in the following references may also be used. U.S. Pat. Nos. 8,771,626; 8,779,220; 8,808,659; U.S. Pat. Pub. No. 20100331599; U.S. Pat. Nos. 7,432,408; 9,914,674; U.S. Pat. Pub. No. 20160289138; U.S. Pat. Pub. No. 20140113804; U.S. Pat. Pub. No. 20160167034; U.S. Pat. Pub. No. 20150315095; and U.S. Pat. Nos. 9,567,273; 9,346,042; 9,260,668; 9,096,487; 8,692,048; 8,653,318; 8,633,346; 8,569,561; 8,552,243; and 7,285,698. Each of these is by this reference incorporated herein for the purpose of the ionic liquids disclosed therein.

In the ionic liquids, various relative amounts of the cation(s) and anion(s) may be used. In embodiments, the molar ratio of the cation:anion is in the range of from 1:1 to 4:1.

Known methods may be used to prepare ionic liquids. Other ionic liquids may be commercially available.

Aromatics

Various aromatics may be used as a component of a catalyst composition comprising any of the disclosed haloalkane sulfonic acids, including combinations of different types of aromatics. However, a single type of aromatic may also be used.

The aromatic may be monocyclic having one or more unfused aromatic rings. Each aromatic ring may have various members, e.g., a 5-membered ring, a six-membered ring, etc. Monocyclic aromatics may be unsubstituted, by which it is meant the aromatic contains only carbon and hydrogen and no heteroatoms. Unsubstituted monocyclic aromatics have a single aromatic ring. Monocyclic aromatics may be substituted, by which it is meant an unsubstituted aromatic in which one or more bonds to a carbon(s) or hydrogen(s) are replaced by a bond to non-hydrogen and non-carbon atoms. Non-hydrogen and non-carbon atoms include, e.g., a halogen atom such as F, Cl, Br; O; N; etc. However, substituted monocyclic aromatics also refer to an unsubstituted monocyclic aromatic in which one or more carbon atoms are bonded to an unsubstituted or substituted alkane or another unsubstituted or substituted monocyclic aromatic. The alkane may be linear or branched, have various numbers of carbon atoms, and may be unsubstituted or substituted. "Unsubstituted" means containing only carbon and hydrogen and no heteroatoms. The alkane group may be substituted, by which it is meant an unsubstituted alkane in which one or more bonds to a carbon(s) or hydrogen(s) are replaced by a bond to non-hydrogen and non-carbon atoms. Non-hydrogen and non-carbon atoms include, e.g., a halogen atom such as F, Cl, Br, and I. Thus, monocyclic aromatics include benzene, biphenyl, triphenyl, furan, pyridine, pyrrole, etc. (each which may be unsubstituted or substituted).

Figure 3:
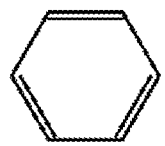
FIG. 3 shows illustrative aromatics for use in catalyst compositions comprising the present haloalkane sulfonic acids.
Figure 3:
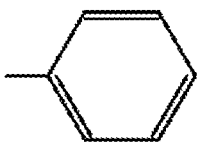
Figure 3:
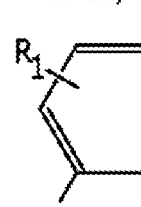
Figure 3:
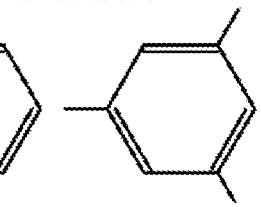
Figure 3:
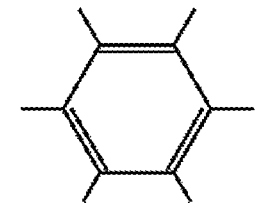

The monocyclic aromatic may have the formula $C_6R_6$, wherein each R is independently selected from hydrogen, a halogen, and an alkyl group. The alkyl group may be linear or branched have various numbers of carbon atoms and may be unsubstituted or substituted as described above with respect to alkyl groups in "Acids." Illustrative such monocyclic aromatics are shown in FIG. 3.

Polycyclic aromatics may be used. Polycyclic aromatics have fused aromatic rings (e.g., two, three, etc. rings). Each ring may have various members and may be unsubstituted or substituted as described for monocyclic aromatics. Naphthalene, anthracene, phenanthrene, benzofuran are illustrative polycyclic aromatics.

The aromatic used may be one which forms, in situ, an ionic liquid when combined with the haloalkane sulfonic acid in forming the catalyst composition.

Lewis Acids

Various Lewis acids may be used as a component of a catalyst composition comprising any of the disclosed haloalkane sulfonic acids, including combinations of different types of Lewis acids. However, a single type of Lewis acid may also be used. The Lewis acid may be a metal salt. Illustrative metal salts include $AlCl_3$, $ZnCl_2$, $FeCl_3$, $GaCl_3$, $InCl_3$, $CuCl$, and $BiCl_3$. The Lewis acid may be a metal-containing ionic liquid that behaves as a Lewis acid, including any such ionic liquids described above.

Bases

Figure 1E:
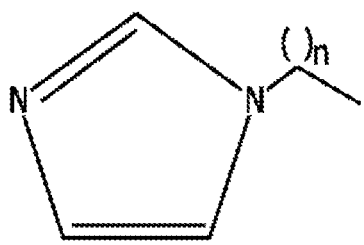
FIG. 1E shows illustrative bases which may be combined with the present haloalkane sulfonic acids to form an ionic liquid.
Figure 1E:
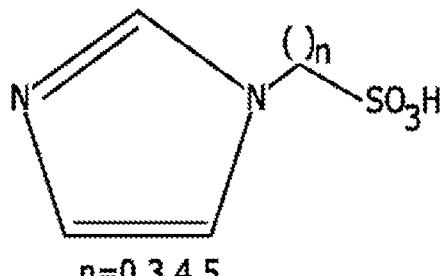
Figure 1E:
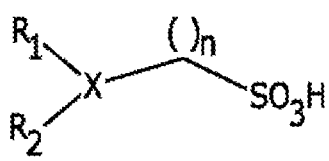
Figure 1E:
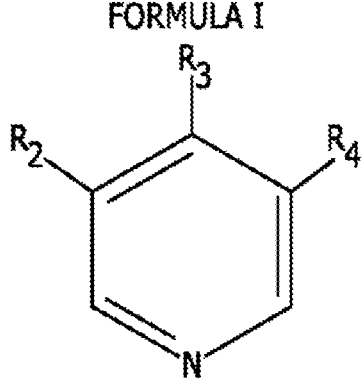
Figure 1E:
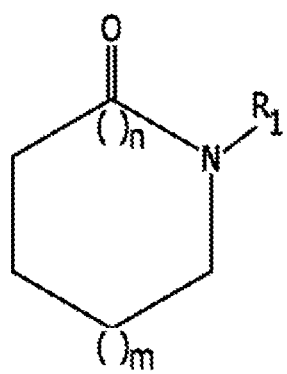

In embodiments, a base is used which forms, in situ, an ionic liquid when combined with any of the disclosed haloalkane sulfonic acids. Thus, any base which generates any of the cations described in "Ionic Liquids," above, upon combination with any of the disclosed haloalkane sulfonic acids may be used. By way of illustration, the base may be an imidazole, an ammonia, a phosphine, a sulfide, a pyridine, or a lactam. The base be selected from the group of compounds having any of the formulae shown in FIG. 1E, i.e., Formulae F-J. In these formulae, the alkyl group may be as defined above with respect to sulfonate in "Ionic Liquids." Different types of bases may be used or a single type of base.

As noted above, one or more of any of the disclosed ionic liquids, aromatics, Lewis acids, and bases may be combined with one or more of any of the disclosed haloalkane sulfonic acids to form a catalyst composition. As also noted above, ion exchange generally occurs between the various components of the catalyst compositions, once formed. In addition, there may be some overlap between compounds suitable for the various components, e.g., some compounds may be suitable as a base and an aromatic. However, catalyst compositions described as comprising, e.g., a "haloalkane sulfonic acid," an "ionic liquid," and an "aromatic" refer to catalyst compositions in which separate and distinct chemicals have been combined to form the catalyst composition regardless of how the various ions may subsequently rearrange/associate therein. For example, a catalyst composition described as comprising a "haloalkane sulfonic acid," an "ionic liquid," and an "aromatic" means that a chemically distinct haloalkane sulfonic acid, a chemically distinct ionic liquid, and a chemically distinct aromatic were combined to form the catalyst composition. As another example, a catalyst composition described as comprising a haloalkane sulfonic acid and an ionic liquid refers to compositions in which a chemically distinct haloalkane sulfonic acid and a chemically distinct ionic liquid were combined to form the catalyst composition.

The particular component or combination of components may be selected to achieve certain behavior in a catalytic conversion reaction, e.g., desired conversion or desired product selectivity. Similarly, the components may be present at various amounts selected to achieve certain behavior.

Referring back to Table 1, in the compositions $[IL]_x$-[Haloalkane Sulfonic Acid]$_{100-x}$, [Lewis Acid]$_x$-[Haloalkane Sulfonic Acid]$_{100-x}$, and [Base]$_x$-[Haloalkane Sulfonic Acid]$_{(100-x)}$, the parameter x refers to a weight (wt) %, i.e., ((weight of the ionic liquid/Lewis acid/base)/(combined weight of the ionic liquid/Lewis acid/base and the haloalkane sulfonic acid))*100. In embodiments, x is in a range of from 0.5 wt % to 90 wt % and the haloalkane sulfonic acid is present at an amount in a range of from 99.5 wt % to 10 wt %. This includes embodiments in which the ionic liquid/Lewis acid/base is present at an amount in a range of from 2 wt % to 80 wt %, from 5 wt % to 60 wt %, from 5 wt % to 30 wt % or 5 wt % to 20 wt % and the haloalkane sulfonic acid is present at an amount in a range of from 98 wt % to 20 wt %, from 95 wt % to 40 wt %, 95 wt % to 70 wt % or 95 wt % to 80 wt %, respectively.

In the compositions $[IL]_x$-[Haloalkane Sulfonic Acid]$_{(100-x)}$-[Aromatic]$_y$ and [Base]$_x$-[Haloalkane Sulfonic Acid]$_{(100-x)}$-[Aromatic]$_y$, x is as defined above and y refers to ((weight of the aromatic)/(combined weight of the ionic liquid/base and haloalkane sulfonic acid))*100. In embodiments, the aromatic component may be present in any amount up to its saturation point in the composition. In embodiments, y is in a range of from of 0.1 wt % to 25 wt %. This includes from 1 wt % to 15 wt %, 1 wt % to 10 wt %, from 3 wt % to 9 wt %, or from 5 wt % to 8 wt %. In embodiments, y may be in a range of from 0.1 wt % to 100 wt % or from 0.1 wt % to 50 wt %.

An amount of water may be present in the catalyst composition. However, in embodiments, the catalyst composition consists or consists essentially of the components of Table 1.

Other components may be included in the catalyst compositions such as multi-ammonium salts/surfactants described in R. Kore, B. Satpati, R. Srivastava, *Synthesis of Dicationic Ionic Liquids and their Application in the Preparation of Hierarchical Zeolite Beta, Chemistry—A European Journal,* 17 (2011) 14360-14365 and R. Kore, R. Srivastava, B. Satpati, *ZSM-5 zeolite nanosheets with remarkably improved catalytic activity synthesized using a new class of structure directing agents, Chemistry—A European Journal,* 20 (2014) 11511-11521, both of which are hereby incorporated by reference in their entirety.

The catalyst compositions may be made by combining the desired components (together or sequentially) at the desired relative amounts. The synthesis may be carried out while stirring and under room temperature.

With regards to catalyst compositions comprising three components, a haloalkane sulfonic acid, an aromatic, and either an ionic liquid or a base which forms, in situ, an ionic liquid with the haloalkane acid, the following is noted. Without wishing to be bound to any particular theory, it is believed that the three components (or ions generated from the three components) may associate to form a molecular complex having unique, synergistic properties, as distinguished from a simple mixture of the individual components. In the present disclosure, terms such as "ternary complex," "clathrate," and the like may be used to describe this molecular complex. However, such terms are not intended to limit the scope of structural form of the molecular complex or catalyst composition. The term "ternary mixture" may also be used in reference to such a catalyst composition. Catalyst compositions comprising two components, e.g., a haloalkane sulfonic acid and an ionic liquid may be referred to as "binary mixtures."

Methods of Using the Haloalkane Sulfonic Acids and Catalyst Compositions Thereof The applications for the disclosed haloalkane sulfonic acids and catalyst compositions thereof are not particularly limited. The haloalkane sulfonic acids may be used by themselves in a variety of processes requiring an acid. The haloalkane sulfonic acids may also be used to provide an ionic liquid, e.g., in combination with any of the disclosed bases or aromatics as noted above. Thus, applications requiring an ionic liquid are also encompassed. Finally, any of the disclosed catalyst compositions may be used in a variety of processes requiring an acidic catalyst composition. Illustrative applications are described below.

Alkylation

The present haloalkane sulfonic acids (and catalyst compositions and ionic liquids formed therefrom, herein after referred to as "related compositions") may be used in an alkylation process to provide an alkylate product for a motor fuel additive. In embodiments, such a method comprises combining a feedstock and any of the disclosed haloalkane sulfonic acids/related compositions under conditions to produce the alkylate product. The feedstock may comprise an alkane and an olefin. The alkane may have four or more carbons, i.e., a C4 alkane. The alkane may be an isoalkane. The olefin may have four carbons, i.e., a C4 olefin, but olefins having other numbers of carbons may be used, e.g., C3, C5, C6. The olefin may be an iso-olefin. The feedstock may comprise isobutane and butene, e.g., 2-butene. Other alkanes and olefins may be used, e.g., propane, pentane, propene, isobutene, 1-butene, trans-2-butene, cis-2-butene, pentenes, amylenes, etc. The feedstock may comprise different types of alkanes and different types of olefins. However, a single type of alkane and a single type of olefin may also be used. Under the appropriate conditions, the alkane(s) and olefin(s) of the feedstock are converted into an alkylate product for a motor fuel additive comprising a mixture of branched alkanes. The method may further comprise recovering the alkylate product from the reaction mixture (the combined feedstock and haloalkane sulfonic acids/related composition).

The conditions under which alkylation occurs refer to parameters such as the amount of the haloalkane sulfonic acid/related composition used, the amount of feedstock used, the reaction temperature, the reaction time, and the reaction pressure. These parameters may be adjusted to provide desired alkylation behavior, e.g., a desired conversion, C8 selectivity, and T/D ratio.

A variety of reactor systems may be used to carry out the alkylation process, including batch, semi-continuous, continuous, and spray reactor systems.

The present haloalkane sulfonic acids/related compositions and alkylation reactions may be characterized as being capable of achieving certain properties or results, including a percent conversion, a percent C8 selectivity, and a T/D ratio. Known methods may be used to calculate these values, e.g., see U.S. Pat. Pub. No. 20100331599, which by this reference is incorporated herein in its entirety. In embodiments, the conversion is at least 95%, at least 99%, at least 99.5%, or at least 100%. In embodiments, the C8 selectivity is at least 75%, at least 80%, at least 85%, at least 90%, or at least 98%. In embodiments, the T/D ratio is at least 10, at least 15, at least 20, at least 25, at least 30, or at least 60. These properties may be referenced with respect to a particular set of reaction conditions and may refer to using a pure isobutane and 2-butene feedstock.

The alkylate product formed is also encompassed by the present disclosure. Gasoline comprising the alkylate product is also encompassed.

LAB Process

The present haloalkane sulfonic acids/related compositions may be used in a process to alkylate benzene. In embodiments, such a process comprises combining benzene, an olefin, and any of the disclosed haloalkane sulfonic acids/related compositions under conditions to produce a linear alkylbenzene. Under the appropriate conditions, the present haloalkane sulfonic acids/related compositions can catalyze the addition of the olefin(s) to benzene to provide an alkylbenzene(s). The process may further comprise recovering the alkylbenzene(s) from the reaction mixture. Here, "benzene" refers both to unsubstituted benzene and substituted benzene. Substituted benzene refers to "monocyclic aromatic" as described above in "Aromatics," except that at least one R is not hydrogen. Substituted benzene also refers to "polycyclic aromatics" as described above in "Aromatics." The olefin may be a mono-olefin, including a linear alpha olefin. The number of carbon atoms in the olefin may be in the range of from 10 to 13. As with "benzene," here, "olefin" refers both to unsubstituted olefin and substituted olefin, with the terms "unsubstituted" and "substituted" having meanings analogous to "alkyl" as described above in "Aromatics." Different types of olefins may be used in the process, i.e., a mixture of different types of olefins.

It is noted that the benzene to be alkylated may itself form a ternary complex with the haloalkane sulfonic acid and an ionic liquid/base in a catalyst composition used for the alkylation. However, when a catalyst composition is used for the alkylation which comprises any of the disclosed haloalkane sulfonic acids, an aromatic, and an ionic liquid or a base, the aromatic and the base, if present, are distinct chemical entities from the benzene to be alkylated. This means that either the aromatic/base are different chemical compounds from the benzene to be alkylated (i.e., are not benzene) or are the same chemical compound, but included separately at a separate amount in the catalyst composition.

The conditions under which the alkylation of benzene occurs refer to parameters such as the amount of the haloalkane sulfonic acids/related compositions, the ratio of benzene:olefin, the reaction temperature, and the reaction time. These parameters may be adjusted to provide, e.g., a desired conversion and/or desired product selectivity. A variety of reactor systems may be used, including batch, semi-continuous, continuous, and spray reactor systems.

The present haloalkane sulfonic acids/related compositions and alkylation processes may be characterized as being capable of achieving certain properties or results, including a percent conversion and a percent selectivity (for a particular product). Known methods may be used to calculate these values. In embodiments, the conversion is at least 95%, at least 98%, at least 99%, at least 99.5%, at least 99.9% or at least 100%. In embodiments, the selectivity for adding the olefin to benzene at its second carbon (e.g., 2-LAB) is at least 30%, at least 35%, at least 40%, at least 50%, or at least 60%. These properties may be referenced with respect to a particular set of reaction conditions.

Acylation Process

The present haloalkane sulfonic acids/related compositions may be used in a process to acylate an aromatic compound. The phrase "aromatic compound" is used to distinguish an aromatic that may be present in a haloalkane sulfonic acid-based composition. It is noted that the aromatic compound to be acylated may itself form a ternary complex with a haloalkane sulfonic acid and an ionic liquid/base in a catalyst composition used for the acylation. In embodiments, a catalyst composition is used for the alkylation which comprises any of the disclosed haloalkane sulfonic acids, an aromatic, and an ionic liquid or a base, the aromatic and the base, if present, are distinct chemical entities from the aromatic compound to be acylated. This means that either the aromatic/base are different chemical compounds from the aromatic compound to be acylated (i.e., are not the same chemical compound) or are the same chemical compound, but included separately at a separate amount in the catalyst composition.

In embodiments, a process to acylate an aromatic compound comprises combining an aromatic compound, an acylating agent, and any of the disclosed haloalkane sulfonic acids/related compositions under conditions to induce acylation of the aromatic compound. Under the appropriate conditions, the present haloalkane sulfonic acids/related compositions can catalyze the addition of an acyl group from the acylating agent to the aromatic compound (i.e., induce acylation). As further described below, the aromatic compound may be substituted and the acyl group may be added to the aromatic compound at its para position. The process may further comprise recovering the acylated aromatic compound from the reaction mixture.

The aromatic compound can have formula:

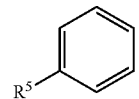

wherein $R^5$ is H, halogen, hydroxyl, substituted or unsubstituted $C_1$-$C_8$ alkyl, or substituted or unsubstituted $C_1$-$C_8$ cycloalkyl. In embodiments, $R^5$ is substituted or unsubstituted $C_1$-$C_8$ alkyl. In embodiments, $R^5$ is unsubstituted $C_1$-$C_8$ alkyl. In embodiments, $R^5$ is unsubstituted $C_4$-$C_6$ alkyl. In embodiments, $R^5$ is isobutyl. In embodiments, the aromatic compound is isobutylbenzene. Unsubstituted alkyl/cycloalkyl means the group contains only carbon and hydrogen and no heteroatoms. Substituted alkyl/cycloalkyl refers to the unsubstituted group in which one or more bonds to a carbon(s) or hydrogen(s) are replaced by a bond to non-hydrogen and non-carbon atoms. Non-hydrogen and non-carbon atoms include, e.g., a halogen atom such as F.

The acylating agent can be an acyl halide of formula:

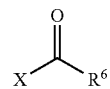

wherein X is a halogen; and $R^6$ is H, halogen, hydroxyl, substituted or unsubstituted $C_1$-$C_8$ alkyl, substituted or unsubstituted $C_1$-$C_8$ cycloalkyl, or substituted or unsubstituted aryl. Unsubstituted and substituted alkyl/cycloalkyl have been defined above with respect to the aromatic compound. Aryl groups may be monocyclic or polycyclic as described in "Aromatics" above and may be unsubstituted or substituted as described with respect to alkyl/cycloalkyl groups. However, substituted aryl groups also refer to an unsubstituted monocyclic aryl group in which one or more carbon atoms are bonded to an alkane. The alkane may be linear, have various numbers of carbon, and may be unsubstituted or substituted as described with respect to alkyl/cycloalkyl groups.

In embodiments, X is chloride. In embodiments, $R^6$ is substituted or unsubstituted $C_1$-$C_8$ alkyl. In embodiments, $R^6$ is unsubstituted $C_1$-$C_8$ alkyl. In embodiments, $R^6$ is unsubstituted $C_1$-$C_4$ alkyl. In embodiments, $R^6$ is methyl. In embodiments, the acylating agent is acetyl chloride.

The acylating agent can be an acid anhydride of formula:

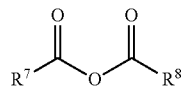

wherein $R^7$ and $R^8$ are independently H, halogen, hydroxyl, substituted or unsubstituted $C_1$-$C_8$ alkyl, substituted or unsubstituted $C_1$-$C_8$ cycloalkyl, substituted or unsubstituted aryl, or wherein, as valence permits, $R^7$ and $R^8$, together with the atoms to which they are attached, form a 4-10 membered cyclic moiety. Unsubstituted and substituted alkyl/cycloalkyl have been defined above with respect to the aromatic compound and unsubstituted and substituted aryl groups have been defined above with respect to the acyl halide.

In embodiments, $R^7$ and $R^8$ are independently H, halogen, hydroxyl, or substituted or unsubstituted $C_1$-$C_8$ alkyl. In embodiments, $R^7$ and $R^8$ are independently substituted or unsubstituted $C_1$-$C_8$ alkyl. In embodiments, $R^7$ and $R^8$ are independently unsubstituted $C_1$-$C_8$ alkyl. In embodiments, $R^7$ and $R^8$ are independently unsubstituted $C_1$-$C_4$ alkyl. In embodiments, the acylating agent is acetic anhydride.

Combinations of different types of aromatic compounds and combinations of different types of acylating agents may be used in the process.

The conditions under which acylation is induced refer to parameters such as the amount of the haloalkane sulfonic acid/related composition, the amount of the acylating agent; the amount of the aromatic compound; the reaction temperature; and the reaction time. These parameters may be adjusted to provide, e.g., a desired conversion and/or desired product selectivity. In embodiments, the mole ratio of the catalytic composition (total moles thereof) as compared to the acylating agent (total moles thereof) to be acylated is in a range of from 0.01:1 to 0.5:1. This includes from 0.01:1 to 0.2:1 and from 0.01:1 to 0.1:1. In embodiments, a mole ratio of the catalyst composition to the acylating agent is no more than 0.5:1. This includes no more than 0.2:1 and no more than 0.1:1. However, in other embodiments, the mole ratio may be up to 1:1 or 2:1.

A variety of reactor systems may be used to carry out the acylation process, including batch, semi-continuous, continuous, and spray reactor systems.

The present haloalkane sulfonic acids/related compositions and acylation processes may be characterized as being capable of achieving certain properties or results, including a percent conversion and a percent selectivity (for a particular product). Known methods may be used to calculate these values. In embodiments, the conversion is at least 90%, at least 95%, at least 99% or at least 99.9%. In embodiments, the selectivity for adding an acyl group of an acylating agent to a substituted aromatic compound at its para position is at least 85%, at least 90%, at least 95%, or at least 99%. These properties may be referenced with respect to a particular set of reaction conditions.

Other Applications

Other illustrative applications for the present haloalkane sulfonic acids/related compositions include Beckmann rearrangement reactions, oligomerization reactions, Diels Alder reactions, trans-alkylation of toluene, and Knoevenagel condensation. Conditions which are typically applied when carrying out these reactions may be used.

EXAMPLES

Example 1. One-Step Process for Preparing Haloalkane Sulfonic Acids

The one-step process to form mono- and multi (e.g., di)-haloalkane sulfonic acids is illustrated in FIGS. 4A-4B. The following Examples are based on this one-step process.

Example 1-I: Preparation of 1,2-dichloroethane-1,2-disulfonic acid [CHCl(SO$_3$H)—CHCl(SO$_3$H)] and tetrachloroethane sulfonic acid [CHCl$_2$—CCl$_2$—SO$_3$H] Under Neat Condition In an N$_2$-filled glove box, a 350-mL high pressure round bottom flask, equipped with a stir bar, tetrachloroethylene (18.3 g, 0.11 mol) was reacted with oleum (or fuming sulfuric acid) (5 g, 0.05 mol) under neat condition. After addition, the reaction mixture was heated with magnetic stirring in a temperature-controlled oil bath at 130° C. After 4 days, the flask was removed from oil bath and left to cool on the benchtop. After the reaction, a brown color reaction mixture was analyzed by NMR (($^1$H, $^{13}$C, DEPT-135, DEPT-90, and HSQC) and confirmed that the mixture contained 1,2-dichloroethane-1,2-disulfonic acid and tetrachloroethane sulfonic acid. The excess amount of tetrachloroethylene from the reaction mixture was removed under high vacuum rota-evaporation and further analyzed by NMR. After rota-evaporation, the amount of the mono-halsosulfonic acid decreased. These results confirm that the mono-halosulfonic acid has a lower boiling point and can be separated from the di-halosulfonic acid by distillation. Before rota-evaporation, the mixture had CHCl$_2$—CHCl—SO$_3$H and CHCl(SO$_3$H)—CHCl(SO$_3$H) acids at 30 and 70%, respectively, as confirmed by NMR. After rota-evaporation the mixture had CHCl$_2$—CHCl—SO$_3$H and CHCl (SO$_3$H)—CHCl(SO$_3$H) acids at 20 and 80%, respectively, as confirmed by NMR.

Example 1-II: Preparation of 1,2-dichloroethane-1, 2-disulfonic acid [CHCl(SO$_3$H)—CHCl(SO$_3$H)] and tetrachloroethane sulfonic acid [CHCl$_2$—CCl$_2$—SO$_3$H] Under Neat Condition In an N$_2$-filled glove box, a 350-mL high pressure round bottom flask, equipped with a stir bar, tetrachloroethylene (18.3 g, 0.11 mol) was reacted with oleum (or fuming sulfuric acid) (10 g, 0.1 mol) under neat condition. After addition, the reaction mixture was heated with magnetic stirring in a temperature-controlled oil bath at 130° C. After 4 days, the flask was removed from oil bath and left to cool on the benchtop. After the reaction, a brown color reaction mixture was analyzed by NMR (($^1$H, $^{13}$C, DEPT-135, DEPT-90, and HSQC) and confirmed the mixture contained 1,2-dichloroethane-1,2-disulfonic acid and tetrachloroethane sulfonic acid. The excess amount of tetrachloroethylene from the reaction mixture was removed under high vacuum rota-evaporation and further analyzed by NMR. Again, after rota-evaporation, the amount of the mono-halsosulfonic acid decreased. Before rota-evaporation, the mixture had $CHCl_2$—CHCl—$SO_3$H and $CHCl(SO_3H)$—$CHCl(SO_3H)$ acids at 35 and 65%, respectively, as confirmed by NMR. After rota-evaporation, the mixture had $CHCl_2$—CHCl—$SO_3$H and $CHCl(SO_3H)$—$CHCl(SO_3H)$ acids at 9 and 91%, respectively, as confirmed by NMR.

Example 1-III: Preparation of 1,2-dichloroethane-1, 2-disulfonic acid [$CHCl(SO_3H)$—$CHCl(SO_3H)$] Under Neat Condition In an $N_2$-filled glove box, a 350-mL high pressure round bottom flask, equipped with a stir bar, tetrachloroethylene (41.45 g, 0.25 mol) was reacted with oleum (or fuming sulfuric acid) (2.5 g, 0.025 mol) under neat condition. After addition, the reaction mixture was heated with magnetic stirring in a temperature-controlled oil bath at 130° C. After 4 days, the flask was removed from oil bath and left to cool on the benchtop. The excess amount of tetrachloroethylene from the reaction mixture was removed by decantation (upper layer) and followed by under high vacuum rota-evaporation, giving a dark brown liquid acid mixture. NMR will be used to confirm content and determine amounts of the mono- and di-halosulfonic acids.

Example 1-IV. Preparation of 1,2-dichloroethane-1, 2-disulfonic acid [$CHCl(SO_3H)$—$CHCl(SO_3H)$] and tetrachloroethane sulfonic acid [$CHCl_2$—$CCl_2$—$SO_3H$] Under Neat Condition In an $N_2$-filled glove box, a 350-mL high pressure round bottom flask, equipped with a stir bar, tetrachloroethylene (8.3 g, 0.05 mol) was reacted with oleum (or fuming sulfuric acid) (5 g, 0.05 mol) under neat condition. After addition, the biphasic reaction mixture was heated with magnetic stirring in a temperature-controlled oil bath at 100° C. After 5 days, the flask was removed from oil bath and left to cool on the benchtop to obtain single liquid phase reaction mixture. To separate the acid compounds from the reaction mixture, vacuum distillation setup was used. The reaction mixture was transferred into a 500-mL round bottom flask and then connected flask with vacuum distillation setup (contains distillation head with water condenser, thermometer, 3-way valve collector, liquid nitrogen trap, vacuum pump, and magnetic stirrer with temperature controller). When the magnetic stirrer heating temperature reached 50° C. (boiling temperature=25° C.) and the pressure was held at −30 psig, a first liquid fraction started to reflux and was named as TCES-I. Further, when heating temperature reached 85° C. (boiling temperature=35° C.) and the pressure was held at −30 psig, a second liquid fraction started to reflux and was named as TCES-II. Both fractions were analyzed by NMR. The presence of $CHCl_2$—$CCl_2$—$SO_3H$ in the first fraction (TCES-I) was confirmed. The NMR results for the second fraction (TCES-II) indicated the presence of at least one haloalkane sulfonic acid, one or both of $CHCl(SO_3H)$—$CHCl(SO_3H)$ and $CH(SO_3H)_2$—$CHCl(SO_3H)$. $CH(SO_3H)_2$—$CH(SO_3H)_2$ may also be present.

Example 1-V: Preparation of 1,2-dichloroethane-1, 2-disulfonic acid [$CHCl(SO_3H)$—$CHCl(SO_3H)$] and tetrachloroethane sulfonic acid [$CHCl_2$—$CCl_2$—$SO_3H$] Under Neat Condition In an $N_2$-filled glove box, a 350-mL high pressure round bottom flask, equipped with a stir bar, tetrachloroethylene (16.6 g, 0.1 mol) was reacted with oleum (or fuming sulfuric acid) (10 g, 0.1 mol) under neat condition. After addition, the biphasic reaction mixture was heated with magnetic stirring in a temperature-controlled oil bath at 100° C. After 5 days, the flask was removed from oil bath and left to cool on the benchtop to obtain single liquid phase reaction mixture. To separate the acid compounds from the reaction mixture, vacuum distillation setup was used. The reaction mixture was transferred into a 500-mL round bottom flask and then connected flask with vacuum distillation setup (contains distillation head with water condenser, thermometer, 3-way valve collector, liquid nitrogen trap, vacuum pump, and magnetic stirrer with temperature controller). When the magnetic stirrer heating temperature reached 50° C. (boiling temperature=25° C.) and the pressure was held at −30 psig, a first liquid fraction started to reflux and was named as TCES-I. Further, when heating temperature reached 85° C. (boiling temperature=35° C.) and the pressure was held at −30 psig, a second liquid fraction started to reflux and was named as TCES-II. Both fractions were analyzed by NMR. The presence of $CHCl_2$—$CCl_2$—$SO_3H$ in the first fraction (TCES-I) was confirmed. The NMR results for the second fraction (TCES-II) indicated the presence of one or more of $CHCl(SO_3H)$—$CHCl(SO_3H)$, $CH(SO_3H)_2$—$CHCl(SO_3H)$, and $CH(SO_3H)_2$—$CH(SO_3H)_2$. The NMR results for the second fraction (TCES-II) indicated the presence of at least one haloalkane sulfonic acid, one or both of $CHCl(SO_3H)$—$CHCl(SO_3H)$ and $CH(SO_3H)_2$—$CHCl(SO_3H)$. $CH(SO_3H)_2$—$CH(SO_3H)_2$ may also be present.

Example 1-VI: Preparation of 1,2-dichloroethane-1, 2-disulfonic acid [$CHCl(SO_3H)$—$CHCl(SO_3H)$] and tetrachloroethane sulfonic acid [$CHCl_2$—$CCl_2$—$SO_3H$] Under Neat Condition In an $N_2$-filled glove box, a 350-mL high pressure round bottom flask, equipped with a stir bar, tetrachloroethylene (33.2 g, 0.2 mol) was reacted with oleum (or fuming sulfuric acid) (20 g, 0.2 mol) under neat condition. After addition, the biphasic reaction mixture was heated with magnetic stirring in a temperature-controlled oil bath at 100° C. After 5 days, the flask was removed from oil bath and left to cool on the benchtop to obtain a single liquid phase reaction mixture. To separate the acid compounds from the reaction mixture, vacuum distillation setup was used. The reaction mixture was transferred into a 500-mL round bottom flask and then connected flask with vacuum distillation setup (contains distillation head with water condenser, thermometer, 3-way valve collector, liquid nitrogen trap, vacuum pump, and magnetic stirrer with temperature controller). When the magnetic stirrer heating temperature reached 50° C. (boiling temperature=25° C.) and the pressure was held at −30 psig, a first liquid fraction started to reflux and was named as TCES-I. Further, when heating temperature reached 85° C. (boiling temperature=35° C.) and the pressure was held at −30 psig, a second liquid fraction started to reflux and was named as TCES-II.

The procedures above may be repeated as follows: 1,2-dichloroethane-1-sulfonic acid may be prepared by following the procedure of Example 1-I, using 1,2-dichloroethene instead of tetrachloroethylene during the synthesis; 1,2-dichlorobutane-1-sulfonic acid may be prepared by following the procedure of Example 1-I, using 1,2-dichlorobutene instead of tetrachloroethylene during the synthesis; tetrabromoethane sulfonic acid may be prepared by following the procedure of Example 1-I, using tetrabromoethylene instead of tetrachloroethylene during the synthesis; tetraiodoethane sulfonic acid may be prepared by following the procedure of Example 1-I, using tetraiodoethylene instead of tetrachloroethylene during the synthesis; 1,2-dichloro 1,2-difluoroethane sulfonic acid may be prepared by following the procedure of Example 1-I, using dichloro difluoro ethylene instead of tetrachloroethylene during the synthesis; hexachloropropane sulfonic acid may be prepared by following the procedure which was adopted in Example 1-I using perchloroprop-1-ene instead of tetrachloroethylene during the synthesis; 1-chloropropane-1,2-disulfonic acid may be prepared by following the procedure of Example 1-I, using 1,1,2-trichloropropene instead of tetrachloroethylene during the synthesis; 1-chlorobutane-1,2-disulfonic acid may be prepared by following the procedure of Example 1-I, using 1,1,2-trichlorobutene instead of tetrachloroethylene during the synthesis; 1-chloro-3,3,3-trifluoropropane-1,2-disulfonic acid may be prepared by following the procedure of Example 1-I, using 1,1,2-trichloro-3,3,3-trifluoropropene instead of tetrachloroethylene during the synthesis.

Example 2. Preparation of Binary/Ternary Mixtures of an Acid, an Ionic Liquid, and an Aromatic Example 2.1-I: Preparation of ($[C_1C_4im][HSO_4])_{10}$-(TCES-II)$_{90}$ In a 20 mL high pressure glass tube, equipped with a stir bar, TCES-II acid (2.25 g (from Example 1-VI) and IL [$C_1C_4im$][$HSO_4$] (0.25 g, commercially available) was added at 10:90 wt % and the reaction mixture was stirred at room temperature for 5 min, giving a liquid double salt IL ($[C_1C_4im][HSO_4])_{10}$-(TCES-II)$_{90}$.

Example 2.2-I: Preparation of ($[C_1C_4im][HSO_4])_{10}$-(TCES-II)$_{90}$-(Mesi)$_1$ Clathrate In a 20 mL high pressure glass tube, equipped with a stir bar, TCES-II acid (2.25 g) and IL [$C_1C_4im$][$HSO_4$] (0.25 g, commercially available) was added at 10:90 wt % and mixed by handshake. After a minute, 1 wt % of mesitylene (0.025 g) was added and the reaction mixture was stirred at room temperature for 5 min, giving a liquid double salt IL clathrate ($[C_1C_4im][HSO_4])_{10}$-(TCES-II)$_{90}$-(Mesi)$_1$.

Example 2.2-I. Preparation of (TCES-II)$_{100}$-(Mesi)$_5$

In a 20 mL high pressure glass tube, equipped with a stir bar, TCES-II acid (2.5 g) and 5 wt % of mesitylene (0.125 g) was added and the reaction mixture was stirred at room temperature for 5 min, giving a liquid catalyst ((TCES-II)$_{100}$-(Mesi)$_5$.

Example 3. Isobutane/Butene Alkylation Apparatus and Procedure

Isobutane/2-butene alkylations were performed in a 20-mL high pressure glass reactor. Cooling was provided by a recirculating chiller using ethylene glycol. The isobutane and 2-butene were premixed at 90:10 wt ratio and collected in ISCO pump in liquid phase. The gas phase (and also unreacted liquid butene converted into gas phase) was collected in a gas sampling bag (1 Lit). The products were analyzed offline by gas chromatography (GC), equipped with a flame ionization detector, and a DB-5 100 m column (J&W Scientific). Helium was used as the GC carrier gas and as the flame ionization detector (FID) makeup gas. The analysis conditions were: split ratio=50:1, injector temperature=280° C., detector temperature=300° C. carrier gas flow rate=20 sccm. The temperature program for GC analysis was as follows: initial column temperature 30° C./hold for 15 min, 0.5° C./min to 100° C., then 5° C./min to 300° C./hold for 15 min. An alkylate reference standard (Supelco) allowed identification of the trimethylpentanes (TMP) and dimethylhexanes (DMH). The GC area percent was equated to weight percent since all hydrocarbons in the reactor effluent had response factors close to unity. The combined mass of TMP and DMH is referred to as the "alkylate product". The gas phase was also analyzed by GC and the butene conversion was calculated.

All experiments were performed in batch. A typical experiment began with the addition of the catalyst into the 20-mL high pressure glass reactor. The reactor was sealed and cooled to the desired temperature. The desired amount of hydrocarbon feed was pumped into the reactor at a flow rate of 1 mL/min while stirring the liquid phase. After a certain reaction time (5-20 min), stirring was stopped and the gas phase was collected in the gas sampling bag quickly. The unreacted liquid hydrocarbon was converted into the gas phase by waiting for approximately 1-3 min and collecting in the same sampling bag.

The results are shown in Table 2, below.

TABLE 2

Isobutane Alkylation Results.

| Catalyst | Cat. Amt | $C_4$ Feed | T/time | P (psig) | Conv. (%) | Liquid Product Selectivity (%) | | | | | | T/D Ratio |
|---|---|---|---|---|---|---|---|---|---|---|---|---|
| | | | | | | $C_5$ | $C_6$ | $C_7$ | $C_8$ | $C_9$ | $C_{10}{}^+$ | |
| $H_2SO_4$ | 2.5 g | 5 mL | 5 C./10 min | 40 | >99.9 | 2.8 | 4.7 | 5.2 | 55.3 | 14.9 | 17.2 | 6.6 |
| TCES-II | 2.5 g | 5 mL | 10 C./20 min | 60 | 84.9 | 10.3 | 5.5 | 6.3 | 58.3 | 14.9 | 4.7 | 3.0 |
| TCES-II Reused | 2.5 g | 5 mL | 10 C./20 min | 50 | 85.8 | 4.3 | 0.9 | 35.3 | 49.9 | 4.0 | 5.8 | 5.9 |
| TCES-II | 2.5 g | 5 mL | 15 C./5 min | 70 | 71.7 | 1.8 | 4.6 | 7.5 | 73.3 | 9.7 | 3.3 | 2.1 |
| TCES-II Reused | 2.5 g | 5 mL | 15 C./5 min | 60 | 70 | 0.8 | 0.8 | 8.6 | 84.5 | 3.1 | 2.2 | 5.4 |
| TCES-II | 2.5 g | 5 mL | 15 C./10 min | 70 | 82.8 | 10.5 | 5.9 | 7.3 | 64.1 | 7.4 | 4.8 | 2.1 |
| TCES-II Reused | 2.5 g | 5 mL | 15 C./10 min | 60 | 82.6 | 6.4 | 1.5 | 22.6 | 64.9 | 2.5 | 2.2 | 4.4 |
| TCES-II | 2.5 g | 5 mL | 15 C./15 min | 70 | 83.2 | 6.0 | 4.8 | 6.8 | 73.1 | 6.3 | 3.0 | 2.4 |
| TCES-II Reused | 2.5 g | 5 mL | 15 C./15 min | 60 | 82.8 | 2.9 | 0.5 | 29.3 | 59.9 | 3.8 | 3.6 | 3.6 |

TABLE 2-continued

Isobutane Alkylation Results.

| Catalyst | Cat. Amt | $C_4$ Feed | T/time | P (psig) | Conv. (%) | Liquid Product Selectivity (%) | | | | | | T/D Ratio |
|---|---|---|---|---|---|---|---|---|---|---|---|---|
| | | | | | | $C_5$ | $C_6$ | $C_7$ | $C_8$ | $C_9$ | $C_{10}^+$ | |
| TCES-II | 2.5 g | 5 mL | 15 C./20 min | 70 | n.d. | 15.2 | 7.6 | 7.7 | 44.7 | 20.5 | 4.5 | 1.7 |
| TCES-II Reused | 2.5 g | 5 mL | 15 C./20 min | 55 | n.d. | 3.2 | 1.5 | 5.7 | 81.1 | 5.0 | 3.7 | 7.0 |
| TCES-II | 2.5 g | 5 mL | 20 C./20 min | 80 | 84.2 | 16.9 | 8.6 | 8.2 | 38.7 | 21.8 | 5.9 | 1.4 |
| TCES-II Reused | 2.5 g | 5 mL | 20 C./20 min | 60 | 74.2 | 2.2 | 6.9 | 16.9 | 59.5 | 7.9 | 6.5 | 4.6 |
| TCES-II | 1.0 g | 5 mL | 15 C./15 min | 60 | 65 | 3.5 | 3.0 | 9.2 | 78.8 | 3.5 | 2.1 | 5.9 |
| TCES-II | 0.5 g | 5 mL | 15 C./15 min | 60 | 50 | 3.1 | 2.1 | 50.2 | 39.2 | 4.1 | 1.4 | 6.5 |
| TCES-II - 5% mesitylene | 2.5 g | 5 mL | 10 C./20 min | 60 | 83.1 | 6.3 | 4.0 | 6.5 | 66.2 | 10.3 | 6.7 | 4.5 |
| $([C_1C_4im][HSO_4])_{10}$(TCES-II)$_{90}$ | 2.5 g | 5 mL | 10 C./20 min | 55 | 75.2 | 0.8 | 0.3 | 6.4 | 82.4 | 5.7 | 4.3 | 7.9 |

Reaction condition: Catalyst, isobutene-2-butene premixed liquid {5 mL, 10 wt. % of 2-butene} from Matheson, T = ° C., time = min.
Note:
TCES-II = second fraction of fresh acid; TCES-II Reused = Recycled acid.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

If not already included, all numeric values of parameters in the present disclosure are proceeded by the term "about" which means approximately. This encompasses those variations inherent to the measurement of the relevant parameter as understood by those of ordinary skill in the art. This also encompasses the exact value of the disclosed numeric value and values that round to the disclosed numeric value.

The foregoing description of illustrative embodiments of the disclosure has been presented for purposes of illustration and of description. It is not intended to be exhaustive or to limit the disclosure to the precise form disclosed, and modifications and variations are possible in light of the above teachings or may be acquired from practice of the disclosure. The embodiments were chosen and described in order to explain the principles of the disclosure and as practical applications of the disclosure to enable one skilled in the art to utilize the disclosure in various embodiments and with various modifications as suited to the particular use contemplated. It is intended that the scope of the disclosure be defined by the claims appended hereto and their equivalents.

What is claimed is:

1. A single-step process for preparing a haloalkane sulfonic acid or salt thereof, the process comprising combining a haloalkene with oleum or 98% sulfuric acid under conditions to react $H_2SO_4$ with the carbon-carbon double-bond of the haloalkene to convert the haloalkene to a haloalkane sulfonic acid or salt thereof, wherein the haloalkane sulfonic acid comprises an alkyl group, at least one sulfonic acid group, and one or more halogens selected from Cl, Br, I, and F, the haloalkane sulfonic acid having a total number of carbon atoms of from 2 to 9, and wherein if at least one F atom is present, the haloalkane sulfonic acid comprises at least one other halogen selected from Cl, Br, and I.

2. The single-step process of claim 1, wherein the process produces $HCCl_2$—$CCl_2$—$SO_3H$.

3. The single-step process of claim 1, wherein the process produces $HCCl(SO_3H)$—$CHCl(SO_3H)$.

4. The single-step process of claim 1, wherein the process produces both $HCCl_2$—$CCl_2$—$SO_3H$ and $HCCl(SO_3H)$—$CHCl(SO_3H)$.

5. The single-step process of claim 1, wherein the haloalkene is tetrachloroethylene.

6. The single-step process of claim 1, wherein the process produces a mixture of a haloalkane mono-sulfonic acid and a haloalkane multi-sulfonic acid and the process further comprises separating the haloalkane mono-sulfonic acid from the haloalkane multi-sulfonic acid.

7. The single-step process of claim 1, wherein the alkyl group is a linear alkyl group and each halogen is Cl, thereby providing a linear chloroalkane sulfonic acid or salt thereof, wherein a single sulfonic acid group is present, thereby providing a linear, chloroalkane mono-sulfonic acid or salt thereof.

8. The single-step process of claim 1, the haloalkane sulfonic acid having formula $CR_3$—$CR_2$—$SO_3H$, wherein
each R is independently selected from hydrogen, $C_nR'_{(2n+1)}$, $C_nR'_{(2n-1)}$, $SO_3H$, and a halogen selected from Cl, Br, I, and F;
n is 0 to 7;
each R' is independently selected from hydrogen, $SO_3H$, and a halogen selected from Cl, Br, I, and F;
at least one R or at least one R' is the halogen; and
if at least one R or at least one R' is F and a single $SO_3H$ is present, then at least another R or at least another R' is a halogen selected from Cl, Br, and I.

9. The single-step process of claim 8, the haloalkane sulfonic acid having formula $C_nR''_{(2n+1)}$—$CR''_2$—$CR''_2$—$SO_3H$, wherein
n is 0 to 7;
each R'' is independently selected from hydrogen, $SO_3H$, and a halogen selected from from Cl, Br, I, and F;
at least one R'' is the halogen; and
if at least one R'' is F and a single $SO_3H$ is present, then at least another R'' is a halogen selected from Cl, Br, and I.

10. The single-step process of claim 9, wherein each halogen is not F.

11. The single-step process of claim 9, wherein each halogen is Cl.

12. The single-step process of claim 9, wherein each halogen is Cl and the haloalkane sulfonic acid is a linear chloroalkane sulfonic acid or salt thereof.

13. The single-step process of claim 12, wherein a single sulfonic acid group is present, thereby providing a linear, chloroalkane mono-sulfonic acid or salt thereof.

14. The single-step process of claim 1, the haloalkane sulfonic acid having formula $CR_2(SO_3H)$—$CR_2$—$SO_3H$, wherein each R is independently selected from hydrogen, $C_nR'_{(2n+1)}$, $C_nR'_{(2n-1)}$, $SO_3H$, and a halogen selected from Cl, Br, I, and F;

n is 0 to 7;

each R' is independently selected from hydrogen, $SO_3H$, and a halogen selected from Cl, Br, I, and F; and at least one R or at least one R' is the halogen.

15. The single-step process of claim 14, the haloalkane sulfonic acid having formula $C_nR''_{(2n+1)}$—CR''($SO_3H$)—CR''$_2$—$SO_3H$, wherein n is 0 to 7;

each R'' is independently selected from hydrogen, $SO_3H$, and a halogen selected from Cl, Br, I, and F; and at least one R'' is the halogen.

16. The single-step process of claim 15, wherein each halogen is not F.

17. The single-step process of claim 15, wherein each halogen is Cl.

18. The single-step process of claim 15, wherein each halogen is Cl and the haloalkane sulfonic acid is a linear chloroalkane sulfonic acid or salt thereof.

19. The single-step process of claim 1, wherein the haloalkane sulfonic acid is selected from the group consisting of $HCCl_2$—$CCl_2$—$SO_3H$; $HCBr_2$—$CBr_2$—$SO_3H$; $HCCl_2$—$CCl_2$—$SO_3H$; $CH_2Cl$—$CHCl$—$SO_3H$; $CH_3$—$CH_2$—$CHCl$—$CHCl$—$SO_3H$; $HCFCl$—$CFCl$—$SO_3H$; $CCl_3$—$CHCl$—$CCl_2$—$SO_3H$; $CH_2Cl$—$CH_2$—$SO_3H$; $CH_2Cl$—$CCl_2$—$SO_3H$; $CHCl_2$—$CHCl$—$SO_3H$; $CHCl_2$—$CFCl$—$SO_3H$; salts thereof; and combinations thereof.

20. The single-step process of claim 1, wherein the haloalkane sulfonic acid is selected from the group consisting of $HCCl(SO_3H)$—$CHCl(SO_3H)$; $CH_3$—$CH_2$—$CH(SO_3H)$—$CHCl(SO_3H)$; $CH_3$—$CH(SO_3H)$—$CHCl(SO_3H)$; $CF_3$—$CH(SO_3H)$—$CHCl(SO_3H)$; $CH(SO_3H)_2$—$CHCl(SO_3H)$; $CCl_2(SO_3H)$—$CHCl$—$SO_3H$; $CH_3$—$CF(SO_3H)$—$CH_2(SO_3H)$; $CF_3$—$CH(SO_3H)$—$CH_2(SO_3H)$; $CF_3$—$CH(SO_3H)$—$CH(SO_3H)_2$; $CHF(SO_3H)$—$CF(SO_3H)_2$; $CH(SO_3H)_2$—$CCl(SO_3H)_2$; salts thereof; and combinations thereof.

* * * * *